United States Patent [19]

Favstritsky et al.

[11] Patent Number: 4,832,873
[45] Date of Patent: May 23, 1989

[54] PROCESS FOR PRODUCING POLYBROMINATED HIGHER ALKYLBENZENES

[75] Inventors: Nicolai A. Favstritsky, Lafayette; Dennis M. Borden, West Lafayette, both of Ind.

[73] Assignee: Great Lakes Chemical Corporation, West Lafayette, Ind.

[21] Appl. No.: 107,088

[22] Filed: Oct. 9, 1987

[51] Int. Cl.$^4$ .............. C09K 21/00; C07C 17/10; C08C 19/12; C08C 19/14
[52] U.S. Cl. .............. 252/601; 106/18.24; 106/18.25; 106/18.35; 252/609; 260/694; 260/DIG. 24; 524/409; 524/411; 524/412; 524/469; 525/355; 525/356; 570/190; 570/234; 570/247; 570/261
[58] Field of Search .............. 252/601, 609; 260/694, 260/DIG. 24; 570/101, 190, 216, 235, 234, 238, 246, 247, 261, 262; 525/355, 356, 357; 106/18.11, 18.24, 18.25, 18.35; 524/408, 409, 411, 412, 468, 469

[56] References Cited

U.S. PATENT DOCUMENTS

| | | | |
|---|---|---|---|
| 3,850,882 | 11/1974 | Underwood et al. | 260/45.75 R |
| 4,129,551 | 12/1978 | Rueter et al. | 260/45.75 R |
| 4,143,221 | 3/1979 | Naarmann | 525/357 |
| 4,200,703 | 4/1980 | Diebel et al. | 525/357 |
| 4,352,909 | 10/1982 | Barda et al. | 525/157 |
| 4,360,455 | 11/1982 | Lindenschmidt et al. | 525/357 |
| 4,728,463 | 3/1988 | Sutker et al. | 252/609 |

OTHER PUBLICATIONS

Hennion and Anderson. (J. Am. Chem. Soc. 68, 424 [1946]).
Mills and Schneider (Ind Eng. Chem., Prod. Res. Dev. 12(3),160 [1973]).
Lamneck, Jr., (J. Am. Chem. Soc. 76, 1106 [1954]).

Primary Examiner—Howard J. Locker

[57] ABSTRACT

Polybrominated higher alkylbenzenes may be produced by reacting the corresponding hydrocarbon material with bromine chloride in an excess bromine reaction medium in the presence of an antimony halide catalyst.

10 Claims, No Drawings

PROCESS FOR PRODUCING POLYBROMINATED HIGHER ALKYLBENZENES

BACKGROUND OF THE INVENTION

1. Field of the Invention

The present invention relates to the production of flame retardant agents and more particularly to a novel process for producing certain polybrominated higher alkyl benzenes useful in flame retarding various thermoplastic resin systems.

2. Description of the Prior Art

Traditionally, most flame retardants, although efficient in their function of retarding the rate of combustion in a resin system, have a tendency to affect adversely one or more key properties of the resin. For example, many flame retardant additives tend to reduce impact strength of the resin; to migrate from the resin composition, resulting in a phenomena known as "bloomp"; to volatilize from the resin composition; to plasticize the resin composition adversely, thus lowering the heat deflection temperature, etc.

It is therefore essential that flame retardant agents be specifically tailored to the resin system so that, in addition to its role as a flame retardant, the agent will additionally enhance the desirable characteristics of the resin composition. Those skilled in the art well known that the selection of such an application-specific flame retardant is unpredictable at best. Thus, even though a given agent may exhibit utility in a particular resin system, that is no guarantee that this agent will have any uses at all with other resins.

It has been discovered, and is the subject of certain other copending patent applications filed herewith, namely, Ser. Nos. 107,228; 107,236; 107,627; and 107,700, all filed Oct. 9, 1987, that, quite unexpectedly, certain brominated higher alkylbenzenes are capable of functioning in a highly satisfactory manner in a number of unrelated resin systems. It has been generally observed that a high loading of many additive-type flame retardants produces a detrimental effect on the physical properties of the resin. Therefore, the accepted procedure has been to use an additive with high bromine content, thus minimizing its weight content in the resin and consequently reducing is deliterious impact on the resin. Brominated compounds with less than 65% bromine are generally considered of marginal or of no interest because, in order to impart flame retardancy to the resin (say 10 weight percent bromine), at least 16 percent by weight of the additive must be added. In many resins, such high loading of the additive significantly deteriorates the physical properties of the resins. However, in the resin systems to which the present invention has application, the alkyl substituent in the benzene ring imparts desirable properties which compensate for its high loading, especially in ABS. However, the art has not taught a satisfactory process by which such brominated higher alkyl benzenes can be produced.

More particularly, no satisfactory bromination technique exists for the prparation of polybrominated higher alkylbenzenes (alkyl$\geq C_6$), especially mixtures of alkylbenzenes containing high concentrations of secondary alkyl groups. Hennion and Anderson (J. Am. Chem. Soc. 68, 424 [1946]) studied the bromination of a wide variety of alkylbenzenes in liquid bromine medium and a small amount of aluminum catalyst. The authors found that in all cases secondary and tertiary alkyl groups were replaced by bromine. However, methyl and ethyl groups were left intact. Replacing aluminum catalyst with a less vigorous iron powder catalyst led substantially to the same results. Thus, bromination of n-propylbenzene led to pentabromo-n-propylbenzene, while isopropylbenzene yielded hexabromobenzene. Additionally, bromination of sec-amylbenzene; sec-octylbenzene, p-diisopropylbenzene all led to hexabromobenzene as product. The authors concluded that only primary alkyl groups survived the bromination.

Mills and Schneider (Ind. Eng. Chem., Prod. Res. Dev 12 (3), 160 [1973]) described the reaction of bromine chloride with aromatic compounds. They showed that benzene could be successfully brominated by BrCl in chlorinated solvents using ferric chloride and aluminum chloride catalysts. Likewise ethylbenzene was brominated by BrCl to 4-bromoethylbenzene. The authors did not show any examples of polybrominated alkylbenzenes, however. In another article, Lamneck Jr., (J. Am. Chem. Soc. 76, 1106 [1954]) described the preparation of monobromo derivatives of propyl-, isopropyl-, butyl-, isobutyl- and sec-butylbenzenes. The bromination was carried out in acetic acid with no catalyst. However, the described bromination produced only monobrominated alkylbenzenes at relatively poor yield.

Barda, et al. U.S. Pat. No. 4,352,909 disclosed that polystyrene can be brominated to the tribromo level by BrCl in a chlorinated hydrocarbon solvent in the presence of a catalytic amount of a Lewis acid, specifically antimony trichloride. While the patentees teach that tribrominated polystyrene may be obtained under the conditions described, higher levels of nuclear bromination do not appear attainable using the Barda, et al. process.

Underwood, et al. U.S. Pat. No. 3,850,882 discloses a three component flame retardant additive system for polyolefins, especially polypropylene, consisting of (a) among other halogenated materials, a halogenated alkyl benzene of the formula:

where X may be Cl or Br; and Y is a hydrocarbon of 1-20 carbon atoms; a is an integer from 0 to 3; and n is an integer from 3 to 6.

(b) Stannic oxide;

(c) a bis-phenylalkylene hydrocarbon.

The patent does not disclose the synthesis of brominated alkylbenzenes, especially mixtures thereof. Nor does the patent specify whether the included bromoalkylbenzenes are primary, secondary, or tertiary.

Rueter, et al. U.S. Pat. No. 4,129,551 disclosed nonflammable polyester compositions incorporating a phosphorus-containing, multiple component flame retardant additive consisting of:

(a) a triarylphosphine oxide or an aryl or alkyl ester of an arylphosphinic acid;

(b) a nuclear brominated alkylbenzene; and (c) customary auxiliary agents and additives.

Polyester compositions based on such agents contain 0.5-10% by weight of bromine and 0.1-2% by weight of phosphorus. Among the nuclear brominated alkylbenzenes described were compounds of the following formula:

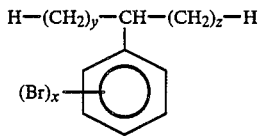

where x = 2 to 5; y and z each are zero or an integer from 1 to 17; and the sum of y+z is an integer between 7 and 17. Mixtures of such compounds are also disclosed. No disclosure is made of the synthesis of brominated alkylbenzenes although the authors suggest that nuclear brominated compounds may be made by known methods as described in the above-described Hennion, et al. and Mills, et al. papers. However, as noted, products produced by these methods yield only brominated primary alkyl benzenes.

Thus, none of the prior art describes a technique for successfully polybrominating higher secondary or tertiary alkylbenzenes or mixtures thereof.

A primary objective of this invention is to provide methods of synthesis of highly brominated higher alkylbenzenes from readily commercially available raw materials.

A related object is to provide methods of the character described that are especially useful in producing polybrominated higher alkylbenzenes.

A further object is to provide methods of the character described useful in producing polybrominated mixtures of secondary and/or tertiary alkylbenzenes.

A still further object is to provide methods for producing mixed liquid polybrominated secondary alkylbenzenes.

Yet a further object is to provide a method for brominating higher alkylbenzenes from the corresponding hydrocarbon materials in excess bromine as a reaction medium utilizing bromine chlroide as the brominating agent and an antimony halide as catalyst.

SUMMARY OF THE INVENTION

The foregoing and other objects, advantages and features of the subject invention may be achieved by reacting a higher $C_{6-18}$ mono- or di-alkylbenzene with bromine chloride in excess bromine as a reaction medium and in the presence of an antimony halide catalyst and thereafter recovering the product thereby produced.

DETAILED DESCRIPTION OF THE PREFERRED EMBODIMENTS

The objectives of this invention may be met in a process for nuclear bromination of higher (i.e., secondary, tertiary and mixtures thereof) mono- and di-alkylbenzenes utilizing bromine chloride as the bromination agent, excess bromine as the reaction medium, and an antimony halide catalyst.

Polybrominated higher alkyl benzenes flame retardant additives produced in accordance with the process of this invention are nuclear halogenated aromatic compounds of the generalized structures (I) and (II):

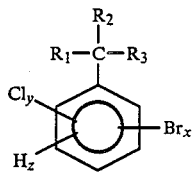

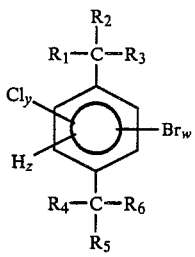

wherein x is 4 or 5; y is zero or 1; z is zero or 1; w is 2 to 4; $R_1$ and $R_4$ are hydrogen or methyl; $R_2$, $R_3$, $R_5$, $R_6$ are alkyl ranging independently from 1 to 16 carbon atoms; and wherein the total number of carbon atoms in each of ($R_1$, $R_2$ and $R_3$) and ($R_4$, $R_5$ and $R_6$) ranges from 5 to 17. Mixtures of such compounds are especially preferred.

Compounds of structure (I) are tetra- and penta-halo secondary and tertiary akylbenzenes, wherein the alkyl group is of 6 to 18 carbon atoms. Compounds of structure (II) are tri- and tetra-halo secondary and tertiary dialkylbenzenes wherein the alkyl group has 6 to 18 carbon atoms.

Preferred compounds produced in accordance with this invention are secondary and tertiary decyl, undecyl, dodecyl tridecyl, tetradecyl benzenes containing 4 to 5 bromines on the benzene nucleus. In place of individual compounds, it is especially preferred to employ mixtures of such compounds. In general, pure brominated primary alkylbenzenes are solids. However, mixtures of brominated secondary and tertiary alkylbenzenes are liquids having a a broader range of uses due to their liquid state. The polybrominated higher alkylbenzenes produced in accordance with this invention generally have a bromine content between 30% and 70% and a chlorine content between 0% and 10%, by weight.

The polybrominated alkylbenzenes produced in accordance with this invention have been found to have utility in a number of distinct resin systems. Favstritsky, et al. United States Patent Application entitled "Flame Retardant ABS Resin Compositions," Favstritsky, et al. United States Patent Application entitled "Flame Retardant PVC" Resin Compositions, Favstritsky, et al. United States Patent Application entitled "Flame Retardant MPPE Resin Composisions," and Favstritsky, et al. United States Patent Application entitled "Flame Retardant Polyurethane Resin Compositions," all filed herewith, disclose and claim respectively flame retardent ABS, PVC and MPPE, and polyurethane compositions incorporating the polybrominated higher alkylbenzene flame retardant agents produced in accordance with the process of this invention.

The polybrominated alkyl benzenes of this invention are produced by the direct bromination of the corresponding unbrominated material using an excess of liquid bromine as the reaction medium, bromine chloride as the brominating agent, and an antimony halide catalyst. It is especially important that the combination of reaction medium, brominating agent and catalyst be selected so as to be sufficiently vigorous that the desired degree of poly-bromination can be achieved without causing the dealkylation of the secondary or tertiary alkyl groups.

In general, the bromine chloride brominating agent is provided in sufficient quantity to yield the desired bromination level in the product. A slight stoichiometric excess in the range of about 0-15 per cent, preferably about 5-12 per cent, is normally provided. The maximum amount of chlorine added should not exceed about 2.55 moles of chlorine per mole of alkyl benzene. The bromine chloride may be added as such to the alkylbenzene starting material, or it may be generated in situ by the addition of chlorine gas to the bromine reaction medium. For reasons of operational convenience, it is preferred to generate the bromine chloride brominating agent in situ in the reaction medium by the subsurface addition of chlorine gas into the agitated reaction mixture. The use of bromine chloride as the brominating agent occasionally results in the incorporation of a small amount of chlorine (e.g., from less than one percent to as much as ten percent depending on the substrate and precise reaction conditions used). It has been found to be useful to minimize the chlorine content, and consistently produce products with less than two percent and typically less than one percent chlorine content.

Liquid bromine is utilized as the reaction medium. Because the mixtures of higher alkylbenzenes are liquids, as are the polybrominated products produced by the process of the present invention, the bromine reaction medium is believed to function primarily to minimize the moderating effect of the unbrominated alkylbenzene and the brominated intermediates and product on the reaction. In general, a large excess of bromine, at least about 100 percent excess and preferably at least about 200 percent excess of that required to generate bromine chloride in situ, is employed.

Antimony halide catalysts are utilized in the process of this invention. More particularly, antimony trichloride, antimony pentachloride, antimony tribromide or antimony metal (in-situ generated antimony halide) may be used with antimony trichloride being preferred. The catalyst is employed in a catalytically effective amount. Preferably, antimony halides are utilized in amounts of at least one mole percent of the alkylbenzene substrate and preferably three to five mole percent of the alkylbenzene substrate. Larger amounts are effective but wasteful.

The temperature and other conditions of reaction are not critical. The reaction may conveniently be conducted at temperatures lying in the range of about $-5°-30°$ C., preferably about $0°-15°$ C. It is especially preferred to conduct the reaction at low temperature (e.g., at or below about $10°-15°$ C.) and to supply cooling to the reaction during the period the brominating agent is added. The reaction is normally conducted at slightly elevated pressures.

The reaction normally proceeds by first adding the catalyst to the excess bromine reaction medium, followed by simultaneous addition of unbrominated higher alkylbenzene substrate and chloride gas (or bromine chloride) to the agitated reaction mixture while the reaction proceeds. Where chlorine gas is added, it is preferably added below the surface of the reaction medium. Other sequences of addition of reactants, reaction medium and catalyst may also be employed, however. For example, the unbrominated, alkylbenzene may be added stepwise over time before chlorine gas is added, the catalyst may be supplied in increments, and the amount of excess bromine reaction medium may be supplemented from time to time during the period of the reaction.

The substrate reacts quickly with the bromine chloride as it is introduced or generated. Thus, as the chlorine addition is stopped in the case of in situ generation, the rate of hydrogen chloride evolution drops to low levels within 15 to 30 minutes.

Upon completion of the reaction, water is added to the reaction mixture to dissolve the catalyst and the bromine is separated by convenient means such as distillation. In the case of hot water assisted distillation as described in the examples, after distilling the excess bromine, separation of the aqueous phase yields the desired secondary alkylbenzene product.

The desired polybrominated higher alkylbenzenes may be produced from the corresponding hydrocarbon materials. Thus, there may be employed as alkylbenzene starting materials compounds of the following structures (III) and (IV):

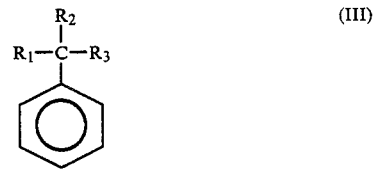
(III)

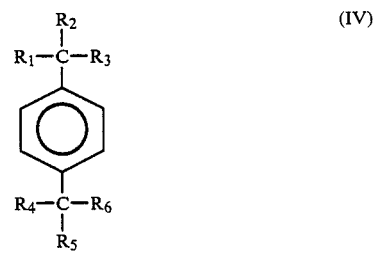
(IV)

wherein $R_1$ and $R_4$ are hydrogen or methyl; $R_2$, $R_3$, $R_5$, $R_6$ are alkyl ranging independently from 1 to 16 carbon atoms; and the total number of carbon atoms in each of ($R_1$, $R_2$ and $R_3$) and ($R_4$, $R_5$ and $R_6$) ranges from 5 to 17. Mixtures of such starting materials may be produced and are especially preferred.

As noted above, it is preferred to produce mixtures of individual polybrominated benzenes in accordance with this invention, and these mixtures may be produced by using mixtures of the corresponding alkyl benzenes. The mixtures of individual polybrominated alkyl benzenes that are most preferred are so-preferred for the additional reason that the corresponding hydrocarbon mixtures are readily available intermediates in the detergent industry.

Especially preferred alkylbenzene staring materials include secondary, straight chain alkylbenzenes of the structure (V):

(V)

where $R_7$ and $R_8$ are independently linear alkyl groups containing 1 to 12 carbon atoms and where, when numerically combined, $R_7$ and $R_8$ contain between 9 and 13 carbon atoms, primarily 9 and 11 carbon atoms and where $R^7$ is about 25 to 35% methyl. A secondary, straight chain alkylbenzene of this type is commercially available from Monsanto Co. under the trademark "Dodane S," which is a mixture of secondary monoalkylbenzenes, wherein the alkyl is primarily undecyl and dodecyl.

Another preferred alkylbenzene starting material in accordance with this invention is a secondary, straight chain alkylbenzene of formula (V), wherein the numerical combination of $R_7$ and $R_8$ is between 9 and 11 carbon atoms and where $R_7$ is about 10 to 15% methyl. Such a preferred alkylbenzene is commercially available from Monsanto Co. under the trademark "Alkylate 215," which is a mixture of secondary monoalkylbenzenes similar to "DODANE S."

Still another preferred starting material is a tertiary, branched chain alkylbenzene of the formula (VI):

(VI)

where $R_9$ and $R_{10}$ are independently alkyl groups containing 1 to 9 carbon atoms and where the numerical combination of $R_9$ and $R_{10}$ is primarily 8 to 11 carbon atoms. Such a tertiary alkyl benzene, in which $R_9$ and $R_{10}$ are typically nonlinear alkyl groups, is commercially available from Monsanto Co. under the trademark "Dodane H," which is a mixture of tertiary branched chain, monoalkylbenzenes, wherein the alkyl is primarily dodecyl.

Yet another preferred starting material is a secondary, straight chain dialkylbenzene of the formula (VII):

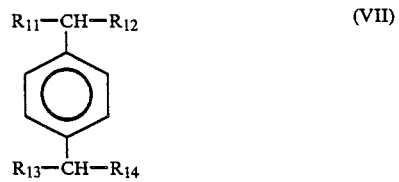

(VII)

where $R_{11}$, $R_{12}$, $R_{13}$, and $R_{14}$ are independently linear alkyl groups containing 1 to 10 carbon atoms and where, when numerically combined, $R_{11}$ and $R_{12}$ or $R_{13}$ and $R_{14}$ contain primarily 11 carbon atoms. Such a material, in which para substitution predominates and which contains up to 10% monoalkylbenzenes, is commercially available from Pilot Chemical Co. under the trademark "Aristol E," which is a mixture of secondary dialkyl benzenes where in alkyl is primarily dodecyl. There are numerous other suppliers of alkylbenzene products which function in this invention. The above are included only as examples of available products.

As noted mixtures of alkylbenzenes are preferred for their availability. However, the bromination of such mixtures requires specialized reaction conditions. The reaction conditions and catalyst of the process of this invention must be strong enough to promote the desired high levels of nuclear bromination and yet mild enough to avoid dealkylation of the benzene nucleus.

More particularly, the principal principles embodied in the present process are the use of:

(1) excess bromine as a solvent. (The substrate itself acts as a solvent and must be counteracted with a large excess of bromine. Solvents other than bromine dilute the brominating strength of the reaction mixture.);

(2) antimony halides as catalysts. (Iron and aluminum catalysts promote the reaction but not without undesirable dealkylation and chlorination);

(3) bromine chloride as the brominating agent. (The bromine/antimony halide combination is not strong enough to brominate the aromatic ring fully whereas the bromine chloride/antimony halide combination in the absence of solvent permits this objective to be achieved).

The process of this invention is illustrated by the following examples, which should not be interpreted to limit the scope of the invention.

EXAMPLE 1

Bromine (1550 grams, 9.7 moles) and antimony trichloride (10 grams, 0.044 moles) were added to a one-liter reactor protected from external moisture. This mixture was cooled to less than 10° C. DODANE S (350 grams, 1.45 moles) was added slowly and continuously over a period of four to five hours. During this same period, 255 grams (3.6 moles) of gaseous chlorine was added slowly and continuously below the surface of the bromine while keeping the temperature of the bromine at or below 10° C. When the addition was complete, water (50 milliliters) was added to dissolve the antimony trichloride. The brominated alkylbenzene, dissolved in bromine, was then added slowly to a three-liter agitated reactor containing two liters of water heated to >90° C. As the mixture was added to the hot water, the bromine was distilled from the reactor and was condensed into a separate vessel for recovery. When the bromine was removed, the water phase was separated to give approximately 880 grams of material containing approximately 60% by weight bromine. The chlorine content is typically less than one percent by weight.

EXAMPLE 2

The procedure of Example 1 was repeated except that "Alkylate 215" was employed in place of "Dodane S." The product weight was approximately 870 grams and contained approximately 61% by weight bromine and 1% by weight chlorine.

EXAMPLE 3

(Comparison)

The procedure of Example 1 was repeated except that "Dodane H" is used in place of "Dodane Sp". The product weight was approximately 860 grams. This material contained approximately 52 percent by weight bromine and approximately 7.5 % by weight chlorine.

EXAMPLE 4

(Comparison)

The procedure of Example 1 was repeated except that the amount of bromine was reduced to 680 grams (4.25 moles). The product weight was approximately 800 grams. This material contained approximately 54% by weight bromine and approximately 3% by weight chlorine.

EXAMPLE 5

(Comparison)

Bromine (760 grams, 4.75 moles) and antimony trichloride (10 grams, 0.044 moles) were added to a one-litPLE 5

(Comparison)

Bromine (760 grams, 4.75 moles) and antimony trichloride (10 grams, 0.044 moles) were added to a one-liter reactor and cooled to less than 10° C. Dodane S (350 grams, 1.45 moles) was added slowly and continuously over a period of two hours while maintaining the temperature less than 10° C. After a one hour hold period, 105 grams of chlorine gas was added slowly and continuously below the surface of the bromine while keeping the temperature below 10° C. The chlorine was added over a period of approximately 1.5 hours. At the end of the chlorine addition, 50 milliliters of water was added to dissolve the antimony trichloride. The product was isolated as described in Example 1. The product weight was approximately 705 grams. The material contained approximately 47% by weight bromine, and the chlorine content was less than 1% by weight.

EXAMPLE 6

(Comparison)

The procedure of Example 1 was repeated except the bromine was increased to 2,200 grams (13.75 moles) and no chlorine was used. Thus, bromine, rather than bromine chloride was used as the bromination agent. The product weighed approximately 570 grams and contained approximately 42% by weight bromine.

EXAMPLE 7

(Comparison)

Bromine (1600 grams, 10 moles) and iron powder (2.8 grams, 0.05 moles) were added to a one liter reactor protected from external moisture. This mixture was cooled to less than 10° C. "Dodane S" 350 grams, 1.45 moles) was added slowly and continuously to this mixture over two hours. Beginning at the same time as the "Dodane S" addition, 278 grams (3.9 moles) of chlorine gas is added subsurface continuously over 2.5 hours while maintaining the reaction at or below 15° C. The product dissolved in bromine was then added slowly to a two liter reactor containing 800 milliliters of water maintained at ≧90° C. After separating the bromine by distillation, 30 grams of 50% aqueous sodium hydroxide were used to precipitate the catalyst. The precipitate is removed by filtration before the water phase was removed to recover the product. The product weight was approximately 790 grams and contained 54% by weight bromine and 3.4% by weight chlorine.

EXAMPLE 8

(Comparison)

The procedure of Example 1 was repeated except that the chlorine was increased from 255 grams to 285 grams (4.0 moles). The product weight was approximately 915 grams. Upon cooling, a solid material precipitated from the product. Approximately 30 grams of this solid was isolated by filtration and was identified as hexabromobenzene. The filtered product contained approximately 60% by weight bromine and approximately 1% by weight chlorine.

EXAMPLE 9

(Comparison)

"Aristol E" (350 grams, 0.85 moles) was added to a one-liter reactor and cooled to less than 10° C. Five grams (0.022 moles) of antimony trichloride was then added. A solution of bromine chloride was prepared in advance by adding elemental bromine to ethylene dichloride in a separate reaction flask, cooling to less than 5° C., and then adding gaseous chlorine. The bromine chloride solution was composed of 440 grams of ethylene dichloride, 250 grams of bromine, and 110 grams of chlorine. The cold solution of bromine chloride was then added slowly and continuously over a period of three hours to the cold dialkylbenzene solution. When the addition was complete, the reaction was allowed to continue for two additional hours at temperatures below 10° C. The antimony trichloride was then dissolved with 50 milliliters of water. The product phase was then cautiously neutralized of any residual bromine chloride with 5% aqueous sodium bisulfite. The ethylene dichloride was then distilled, leaving a product of 545 grams. The product contained approximately 32% by weight bromine and approximately 4% by weight chlorine.

EXAMPLE 10

(Comparison)

Bromine (2400 grams, 15 moles) and iron powder (3.8 grams, 0.068 moles) were added to an agitated two-liter reactor protected from moisture. 1-Phenyloctane (190 grams, 1.0 mole) (available from Aldrich Chemical Co.) was then added to the mixture continuously over eight hours while maintaining a reaction temperature of 15° C. The reaction was then allowed to stand at 25° C. for 18 hours. The excess bromine was then distilled under vacuum at 25° C. The product was then dissolved in methanol to remove catalyst and residual bromine. The crude product weighed 642 grams. After recrystallization from acetone, a white product was recovered which contained about 69% by weight bromine. The product showed a single peak in the gas chromatograph.

EXAMPLE 11

(Comparison)

The procedure of Example 10 was repeated except that "Dodane S" (246 grams, 1.0 moles) was substituted for the 1-phenyloctane. The bromine was removed from the product using the procedure described in Example 7. The product in this case was an unmanageable tar.

A summary of brominations given by Examples 1 to 11 is shown in Table I.

TABLE I

| Example | Material | Procedure | Halogen Contained in Product | | |
|---|---|---|---|---|---|
| | | | Moles Bromine | Moles Chlorine | Total |
| 1 | Dodane S | Standard | 4.5 | — | 4.5 |
| 2 | Alkylate 215 | Standard | 4.5 | 0.2 | 4.7 |
| 3 | Dodane H | Standard | 3.95 | 1.30 | 5.25 |
| 4 | Dodane S | Less bromine | 3.75 | 0.5 | 4.25 |
| 5 | Dodane S | Sequential | 2.65 | — | 2.65 |

TABLE I-continued

| Example | Material | Procedure | Halogen Contained in Product | | |
|---|---|---|---|---|---|
| | | | Moles Bromine | Moles Chlorine | Total |
| 6 | Dodane S | No chlorine addition | 2.0 | — | 2.0 |
| 7 | Dodane S | Iron catalyst | 3.65 | 0.5 | 4.15 |
| 8 | Dodane S | Excess chlorine | 4.6 | 0.2 | 4.8 |
| 9 | Aristol E | BrCl prepared separately | 2.7 | 0.7 | 3.4 |
| 10 | 1-phenyl-octane | Harsh bromination conditions | 5.0 | — | 5.0 |
| 11 | Dodane S | Harsh bromination conditions | — | — | — |

As shown in Table I, Examples 1 and 2 represent optimized or nearly optimized conditions for producing polybrominated secondary alkylbenzenes in accordance with this invention. The subsequent examples demonstrate the effect of changes in substrate, stoichiometry, and reaction conditions, showing that the process defined by this invention is unique.

Example 3 illustrates the effect of employing a tertiary alkylbenzene. The additional steric hinderance of the tertiary alkyl group reduces the number of bromines which can be substituted into the ring. When the bromination reached its maximal level, additional chlorine resulted in ring chlorination. The molecule is also more susceptible to dealkylation and side chain halogenation when the optimal chlorine usage is exceeded. Thus, for tertiary alkylbenzenes, the optimal amount of chlorine needs to be lower than the amount used for secondary alkylbenzenes. These same problems arise with secondary alkylbenzenes when the optimal chlorine or bromine chloride usage is exceeded. Example 4 illustrates that when the excess bromine is reduced, the reaction does not proceed as far. If the excess of bromine were completely eliminated, this effect would be even more pronounced, thereby showing that the use of a substantial bromine excess as a reaction medium is an essential part of the present invention.

Example 5 shows how the substrate itself can be used to moderate the extent of reaction by acting as a solvent and thereby reducing the degree of bromine substitution to an undesirable extent.

Example 6 shows the importance of bromine chloride in reaching high levels of bromination and that bromine itself is not a satisfactory bromination agent in accordance with the present invention.

Example 7 shows that a non-antimony halide catalyst reduces the bromination level and increases the extent of ring chlorination.

Example 8 shows that dealkylation and major yield losses are caused by trying to push the reaction beyond the conditions of Examples 1 and 2 by increasing the chlorine used.

Example 9 shows that attempted bromination of a dialkylbenzene using bromine chloride in ethylene dichloride solvent does not produce the desired results in that an insufficient level of ring bromination and increased ring chlorination are observed.

Example 10 shows that a primary alkylbenzene can survive well under harsh bromination conditions known in the art. Example 11 shows that secondary alkylbenzenes of the type to which this invention is directed are destroyed by these harsh bromination conditions.

The foregoing data demonstrate that secondary and tertiary alkyl benzenes can be brominated under the conditions, catalysts, reaction medium, and brominating agent of this invention. In order to achieve the desired high levels of bromination, substantially free of chlorine, in high yield, and without excessive dealkylation, one must use a large excess of bromine as a solvent, bromine chloride as a brominating agent and antimony halides as catalysts.

We claim:

1. A process for producing tetra- and penta-brominated higher alkylbenzenes comprising the steps of:
   reacting bromine chloride with a higher alkylbenzene, wherein the alkyl group contains 6 to 18 carbon atoms, in an excess of bromine as the sole reaction medium and in the presence of an antimony halide catalyst at a temperature of about 0° to 15° C. for a time sufficient from bromination to reach at least the tetrabromo level; and
   recovering the product thereby produced.

2. A process, as claimed in claim 1 wherein, the product is a compound of the structure:

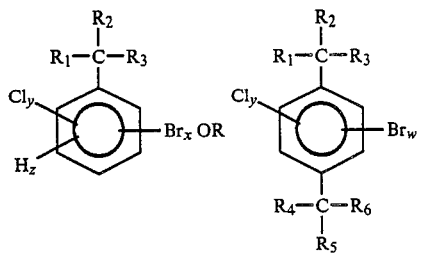

where x is 4 or 5, y is zero or 1, z is zero or 1 and w is 3 or 4; where y plus x equals 4 or 5 and where y plus w equals 4; where $R_1$ and $R_4$ are hydrogen or methyl, and $R_2$, $R_3$, $R_5$, $R_6$ are independently alkyl ranging from 1 to 16 carbon atoms and where the total number of carbon atoms in each of ($R_1$, $R_2$ and $R_3$) and ($R_4$, $R_5$ and $R_6$) ranges from 5 to 17.

3. A process, as claimed in claim 2, wherein the product is a tetra- or penta-bromo secondary $C_6$-$C_{18}$-alkylbenzene.

4. A process, as claimed in claim 2, wherein the product is a tetra-bromo secondary or tertiary di-$C_{6-18}$-alkylbenzene.

5. A process, as claimed in claims 3 or 4, wherein the product comprises a mixture of $C_{10-12}$ alkyl groups.

6. A process, as claimed in claims 3 or 4, wherein the the product is a liquid mixture of $C_{10-12}$ tetra- and penta-bromoalkylbenzenes.

7. A process, as claimed in claim 1, wherein at least about a 100 percent excess of bromine is utilized as the reaction medium.

8. A process, as claimed in claim 1, wherein the antimony halide is antimony trichloride.

9. A process, as claimed in claim 1, wherein the bromine chloride is produced in situ by addition of chlorine gas to the bromine reaction medium.

10. A process, as claimed in claim 1, wherein the polybrominated higher alkylbenzenes comprise about 30 to 70 per cent bromine by weight.

* * * * *

UNITED STATES PATENT AND TRADEMARK OFFICE
CERTIFICATE OF CORRECTION

PATENT NO. : 4,832,873
DATED : May 23, 1989
INVENTOR(S) : Nicolai A. Favstritsky It is certified that error appears in the above-identified patent and that said Letters Patent is hereby corrected as shown below:

Column 1, line 32   "uses should be --use--

Column 1, line 62   "(alkyl $\geqq$ C$_6$)" should be --(alkyl $\geq$ C$_6$)--

Column 2, line 12   "12" should be --$\underline{12}$--

Column 2, line 21   "76" should be --$\underline{76}$--

Column 2, line 58   "disclosed" should be --discloses--

Column 3, line 21   "alkyl benzenes." should be --alkylbenzenes.--

Column 3, line 64   "alkyl benzenes" should be --alkylbenzenes--

Column 4, line 53   "PVC" Resin Composition, Favstritsky" should be --PVC Resin Compositions", Favstritsky--

Column 4, line 55   "Composisions" should be --Compositions--

Column 4, line 63   "alkyl benzenes" should be --alkylbenzenes--

Column 5, line 12   "alkyl benzene" should be --alkylbenzene--

Column 6, line 52   "alkyl benzenes" should be --alkylbenzenes--

UNITED STATES PATENT AND TRADEMARK OFFICE
CERTIFICATE OF CORRECTION

PATENT NO. : 4,832,873

DATED : May 23, 1989

INVENTOR(S) : Nicolai A. Favstritsky

It is certified that error appears in the above-identified patent and that said Letters Patent is hereby corrected as shown below:

Column 6, line 53    "alkyl ben-" should be --alkylben- --

Column 7, line 34    "alkyl benzene" should be --alkylbenzene--

Column 8, line 57    "Dodane Sp" should be --Dodane S--

Column 9, lines 8-12 "chloride (10 grams, 0.044 moles) were added to a one - lit PLE 5 (Comparison) Bromine (760 grams, 4.75 moles) and antimony trichloride (10 grams, 0.044 moles) were added to a one" should be --chloride (10 grams, 0.044 moles) were added to a one--

Column 11, line 26   "hinderance" should be --hindrance--

Column 12, line 4    "alkyl benzenes" should be --alkylbenzenes--

Column 12, line 21   "from bromination" should be --for bromination--

UNITED STATES PATENT AND TRADEMARK OFFICE
CERTIFICATE OF CORRECTION

PATENT NO. :  4,832,873
DATED     :  May 23, 1989
INVENTOR(S) :  Nicolai Favstritsky It is certified that error appears in the above-identified patent and that said Letters Patent is hereby corrected as shown below:

Colum 12, line 24   "in claim 1 wherein, the" should be --in claim 1, wherein the--

Column 12, lines 26-37

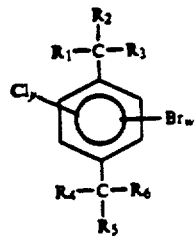  should be  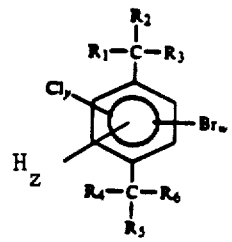

Signed and Sealed this

Eleventh Day of May, 1993

Attest:

MICHAEL K. KIRK

Attesting Officer    Acting Commissioner of Patents and Trademarks